(12) United States Patent
Gauchet

(10) Patent No.: US 6,395,032 B1
(45) Date of Patent: May 28, 2002

(54) INTERVERTEBRAL DISC PROSTHESIS WITH LIQUID CHAMBER

(75) Inventor: Fabien Gauchet, Duvy (FR)

(73) Assignee: DIMSO (Distribution Medicale Du Sud-Ouest) (FR)

(*) Notice: Subject to any disclaimer, the term of this patent is extended or adjusted under 35 U.S.C. 154(b) by 0 days.

(21) Appl. No.: 09/857,657

(22) PCT Filed: Dec. 9, 1999

(86) PCT No.: PCT/FR99/03074

§ 371 (c)(1),
(2), (4) Date: Jun. 7, 2001

(87) PCT Pub. No.: WO00/35386

PCT Pub. Date: Jun. 22, 2000

(30) Foreign Application Priority Data

Dec. 11, 1998 (FR) .............................. 98/15673

(51) Int. Cl.[7] ................................. A61F 2/44
(52) U.S. Cl. .................. 623/17.12; 623/17.11
(58) Field of Search ............................ 623/17.11–17.16

(56) References Cited

U.S. PATENT DOCUMENTS

| 3,867,728 | A | * | 2/1975 | Stubstad et al. | 623/17.12 |
| 3,875,595 | A | * | 4/1975 | Froning | 623/17.15 |
| 4,863,477 | A | | 9/1989 | Monson | 623/17 |
| 4,911,718 | A | * | 3/1990 | Lee et al. | 623/17.15 |
| 4,932,969 | A | | 6/1990 | Frey et al. | 623/17 |
| 5,002,576 | A | * | 3/1991 | Fuhrmann et al. | 623/17.15 |
| 5,071,437 | A | * | 12/1991 | Steffee | 623/17.16 |
| 5,401,269 | A | * | 3/1995 | Buttner-Janz et al. | 623/17.15 |
| 5,534,028 | A | | 7/1996 | Bao et al. | 623/17 |
| 5,674,294 | A | * | 10/1997 | Bainville et al. | 623/17.16 |
| 5,865,846 | A | * | 2/1999 | Bryan et al. | 623/17 |
| 5,888,226 | A | * | 3/1999 | Gogozinski | 623/17.16 |
| 6,052,992 | A | | 4/2000 | Erochenko | 60/509 |
| 6,117,174 | A | * | 9/2000 | Nolan | 623/17.11 |
| 6,136,031 | A | * | 10/2000 | Middleton | 623/17 |
| 6,162,252 | A | * | 12/2000 | Kuras et al. | 623/17.16 |
| 6,187,043 | B1 | * | 2/2001 | Ledergerber | 623/8 |

FOREIGN PATENT DOCUMENTS

| DE | G 90 00 094.3 | 1/1990 |
| WO | WO 96/01598 | 7/1995 |

* cited by examiner

Primary Examiner—Jeffrey A. Smith
Assistant Examiner—Michael B Priddy
(74) Attorney, Agent, or Firm—Lerner, David, Littenberg, Krumholz & Mentlik, LLP

(57) ABSTRACT

An intervertebral disc prosthesis includes two opposing plates and a flexible seal extending between the two plates for forming a closed chamber therebetween. The disc prosthesis also includes a liquid provided in the chamber and a body disposed in the liquid and the chamber, the body having a plurality of pores at an outer surface thereof and cavities extending from the pores into the body. The liquid and the body are selected from materials so that said liquid does not normally wet to said cavities and compressive energy must be applied to the liquid for forcing the liquid into the cavities.

26 Claims, 2 Drawing Sheets

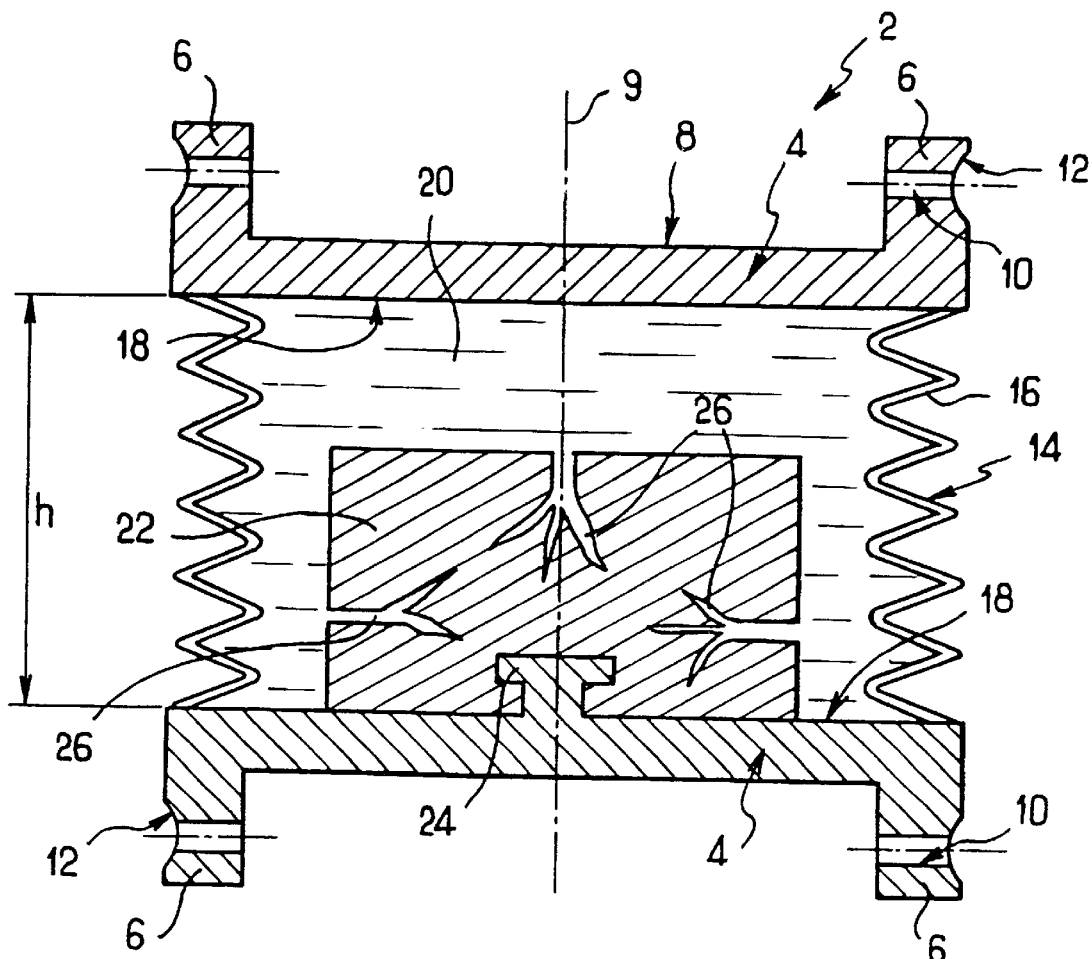
FIG_1
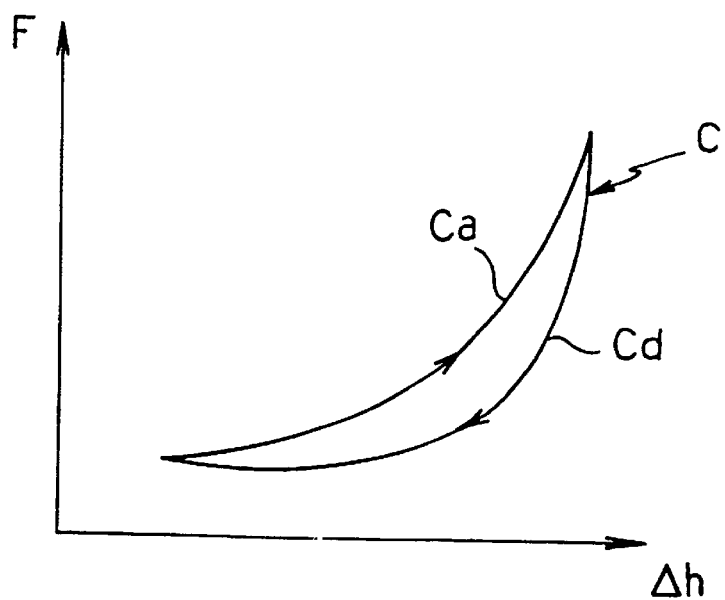
FIG_2

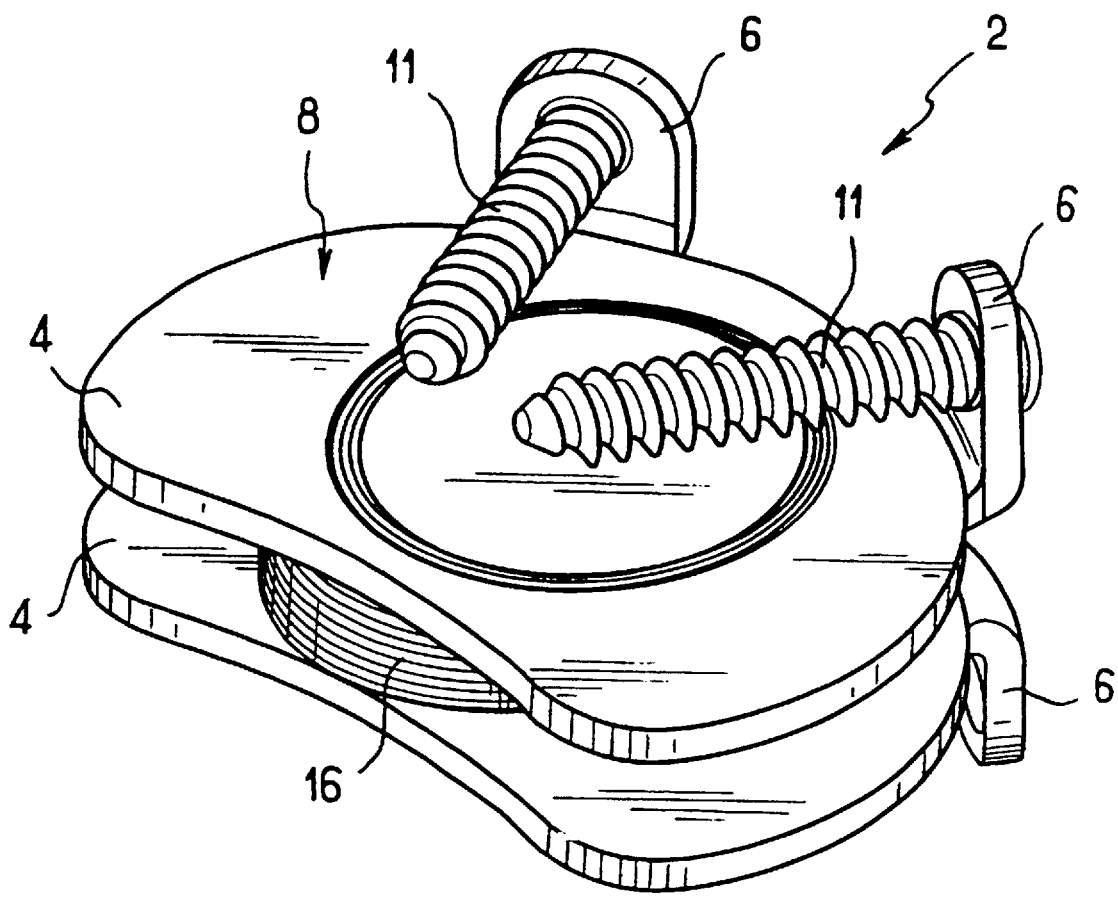
FIG_3

INTERVERTEBRAL DISC PROSTHESIS WITH LIQUID CHAMBER

BACKGROUND OF THE INVENTION

The invention concerns intervertebral disc prostheses.

An intervertebral disc prosthesis intended to replace an intervertebral disc is known, for example, from the document EP-O,277,282. It comprises two plates which are able to bear against the vertebral plates of the vertebrae adjacent to the disc which is to be replaced, and a cushion which is interposed between the plates. The cushion comprises a compressible body and a chamber enclosing a liquid. This prosthesis has the disadvantage that the compressible body is susceptible to wear, which in the long term modifies the mechanical behavior of the prosthesis. Moreover, its friction against the plates causes erosion of particles which can migrate within the patient's body.

U.S. Pat. No. 6,052,992 to Eroshenko discloses a structure for selectively accumulating and dissipating energy. Referring to FIG. 1, the structure includes a porous capillary solid matrix 11 and a liquid 13 that surrounds the porous capillary matrix. The matrix is lyophobic relative to the liquid, i.e., the surface tension is such that the liquid is non-wetting when it comes into contact with the surface of the matrix. The liquid 13 surrounding the porous capillary matrix 11 is selected to define a solid/liquid separation surface having an area that varies isothermally and reversably as a function of the external pressure to which the structure is subjected. As such, the liquid can only be forced into the pores or capillaries when sufficient compression is exerted on the structure. In FIG. 3a, the liquid 13 is present at the entrance to a capillary passage 12 formed in the porous capillary solid matrix 11. The liquid is unable to penetrate into the passage 12, however, forming a meniscus 15. Referring to FIG. 3b, when compressive forces are applied to the structure, the liquid is forced to penetrate into the capillary passage 12. When the pressure applied to the structure is released, spontaneous expansion is obtained to enable a return from the state shown in FIG. 3b to the state shown in FIG. 3a.

SUMMARY OF THE INVENTION

It is an object of the invention to make available a prosthesis whose mechanical behavior is identical over a long period of time, and which reduces the risks of particles being released in the patient's body.

With a view to achieving this object, the invention provides an intervertebral disc prosthesis comprising a compressible cushion having a body made of a material, and a liquid which is able to come into contact with the body, in which the liquid and the material are such that the liquid does not wet the body.

Given that the liquid does not wet the body, the forced contact of the liquid with the body requires a certain energy. This energy is restored in its entirety when the liquid is allowed to separate again from the body. A sort of spring effect is produced in this way. This effect is all the more appreciable as the surface of contact of the liquid with the body is great. The prosthesis can thus take up very substantial stresses, deforming under compression or flexion, and can then produce the inverse deformation by restoring the stored energy. Such a prosthesis can store a considerable quantity of energy in a small volume. In addition, the movement of the liquid in contact with the body does not generate any wear: the prosthesis is thus able to present the same mechanical behavior over a very long period of time. Moreover, the absence of friction between solid parts practically eliminates any risk of release of particles in the body.

The spring effect will be very great in the presence of a porous body, even one of very limited volume.

If the body has cavities communicating with each other along very long networks, the path to be traveled by the liquid upon entry and exit is particularly long. The result of this is that the liquid dissipates some of the energy on account solely of its circulation in the body. Consequently, the whole arrangement can constitute a partial damper. The combination of the spring effect and the damping effect thus means that for the prosthesis the curve representing the compression stress as a function of the variation in length of the prosthesis on its main axis has a hysteresis form, like a healthy natural intervertebral disc. The prosthesis thus comes very close to the mechanical behavior of a real disc.

The prosthesis advantageously comprises two plates which extend either side of the cushion, the body being fixed to at most one of the plates.

Other characteristics and advantages of the invention will become more apparent from the following description of a preferred embodiment which is given as a nonlimiting example.

BRIEF DESCRIPTION OF THE DRAWINGS

FIG. 1 is an axial section through a prosthesis according to the preferred embodiment of the invention;

FIG. 2 is the curve showing the variation in the compression force applied to the prosthesis as a function of the change in its height along its axis; and;

FIG. 3 is a perspective view of the prosthesis from FIG. 1.

DETAILED DESCRIPTION

Referring to FIGS. 1 and 3, the prosthesis 2 comprises two plates 4 having a plane of a generally circular shape or preferably a bean shape with posterior hilum. The two plates are flat and extend parallel to one another, centered on a main axis 9 of the prosthesis perpendicular to the plates.

Each plate 4 has two lugs 6 which project from an outer face 8 of the plate 4 perpendicular to the plane of the plate. Each lug 6 has an orifice 10 passing right through it in the direction of the center of the plate and, on a face of the lug 6 remote from the plate 4, a recess 12 of spherical shape. The orifices 10 can receive a bone screw 11 which has a head whose lower face has a male spherical shape interacting with the female recess 12 on the lug 6 in order to permit free orientation of the screw relative to the associate lug. In FIG. 1, the two lugs 6 of each plate have been brought into the same sectional plane, which is not in reality the case, as is shown in FIG. 3.

For short-term anchoring of the disc prosthesis 2 in the column, the screws 11 can be anchored in the body of the vertebrae adjacent to the disc which is to be replaced.

However, it will be possible to provide for long-term anchoring in which, in addition, the surfaces 8 of the plates 4 in contact with the adjacent vertebrae are covered with hydroxyapatite or any other substance known per se for stimulating bone growth. Before being covered, said surfaces 8 can be treated to obtain a more or less porous surface condition, with anchoring points for the bone tissue, so as to ensure a better interface with said bone tissue.

The prosthesis has a cushion 14 interposed between the plates. This cushion comprises a bellows 16. It has a shape which is symmetrical in revolution about the axis 9. Its wall profile comprises corrugations which make it possible to vary the length of the bellows 16 in the axial direction 9 without appreciably varying the surface area of its cross section transverse to the axis 9. In this case the bellows, like the plates 4, is made of titanium or titanium alloy so that it has a certain degree of axial strength and forms a compression spring. It can also be deformed in a direction perpendicular to the axis 9 or be subjected to torsion about the axis 9 or any axis perpendicular thereto.

At its two axial ends, the bellows 16 has edges which are bonded to respective edges of the plates 4 projecting for example, but in a manner not illustrated, from an inner face 18 of the plates. Said bonding is made leaktight so that the bellows 16 and the two plates 4 define a leaktight chamber of variable volume.

The bellows 16 has for example, in a manner not illustrated, ten convolutions, that is to say eight outer crests in addition to the two crests attached to the plates 4. It has here an external diameter of about 30 mm and an internal diameter of about 17 mm. Its height, when the prosthesis is not loaded, is 10 mm. The wall of the bellows can be made using one, two or three sheets each measuring 0.1 mm in thickness and of which the sum of the thicknesses forms the thickness of the wall. The bellows here has an inherent strength of about 1.6 N/mm.

The chamber delimited by the bellows 16 and the two plates 4 is filled with a liquid 20. The cushion 14 comprises a body 22 which is here anchored to the plane inner face 18 of one of the two plates, for example the lower plate 4 in FIG. 1. For this purpose, a raised part 24 of the plate extends into the body. The shape of the body can be, for example, cylindrical about the axis 9. The body will, for example, be sufficiently narrow perpendicular to the axis 9 so as never to come into contact with the bellows during the deformations of the prosthesis. Likewise, a sufficient free space will be formed between the free end, here the upper end, of the body 22 and the opposite plate so that they never come into mutual contact. The body 22 is surrounded by the liquid which is able to come into contact with it.

The liquid 20 and the material of the body 22 will preferably be biocompatible. They are chosen such that the liquid does not wet the body, that is to say that in the absence of stress for this purpose it tends to remain out of contact with the body. The liquid will be water, for example, and the material of the body will be a biocompatible material such as titanium or a titanium alloy. This material will preferably be porous in order to offer a large area of surface contact with the liquid. Moreover, the cavities of the body constituting its pores will be made to communicate with each other in fairly long networks in order to supply a damping effect in addition to the spring effect. In FIG. 1, the pores or cavities 26 of the body 22 have been illustrated diagrammatically for greater clarity. It goes without saying that these pores are invisible on the scale in FIG. 1 and infinitely more numerous than those illustrated. Thus, with the height h being measured from one plate to the other at the level of the axis 9, the curve in FIG. 2 illustrating the variation in compression F of the prosthesis along its axis 9 as a function of its negative variation in height Δh will have a hysteresis form. Thus, the curve Ca indicating the change in force F when this increases is entirely above the curve Cd illustrating the decrease in force F. This form is due to the combination of the spring effect and the damper effect.

A pocket of gas could also be provided inside the chamber of liquid.

The prosthesis according to the invention is adapted in particular for the lumbar region of the spine.

Many modifications can of course be made to the invention without departing from the scope thereof. The body 22 can be free of any anchoring to the plates. It will thus be free to move spontaneously in relation to each of them. The prosthesis will then be able to be arranged in such a way that, in any position and in any state of stressing of the prosthesis, the body 22 is in contact with at most one of the plates.

The body 22 will be able to have an ellipsoid shape.

What is claimed is:

1. An intervertebral disc prosthesis comprising:

two opposing plates;

a flexible seal extending between said two plates for forming a closed chamber between said two plates;

a liquid provided in said chamber; and a body disposed in said chamber and in said liquid, said body having a plurality of pores at an outer surface thereof and cavities extending from said pores into said body, wherein said liquid and said body are selected from materials so that said liquid does not normally wet to said cavities and compressive energy must be applied to said liquid for forcing said liquid into said cavities.

2. The prosthesis as claimed in claim 1, wherein said cavities are in communication with one another within said body.

3. The prosthesis as claimed in claim 2, wherein said cavities are microscopic.

4. The prosthesis as claimed in claim 1, wherein the energy applied to said liquid is dissipated as said liquid circulates through said cavities of said body.

5. The prosthesis as claimed in claim 2, wherein said two opposing plates are movable relative to one another.

6. The prosthesis as claimed in claim 4, wherein said cavities are adapted to store the energy applied to said liquid when said liquid is forced into said cavities.

7. The prosthesis as claimed in claim 6, wherein said cavities are adapted to release the energy applied to said liquid as said liquid recedes from said cavity.

8. The prosthesis as claimed in claim 7, wherein said body is adapted to store at least some of the energy applied to said liquid therein when said opposing plates move toward one another, and release the at least some of the energy stored therein when said opposing plates move away from one another.

9. The prosthesis as claimed in claim 1, wherein at least one of said plates is securable to bone.

10. The prosthesis as claimed in claim 9, wherein the at least one of said plates securable to bone has at least one lug projecting from a face thereof, said lug having an orifice adapted to receive a screw insertible into the bone.

11. The prosthesis as claimed in claim 1, wherein said body is fixed to one of said plates and movable relative to the other of said plates.

12. The prosthesis as claimed in claim 1, wherein said flexible seal includes a bellows having an upper edge secured to one of said plates and a lower edge secured to the other of said plates.

13. The prosthesis as claimed in claim 1, wherein said flexible seal is made of a material selected from the group consisting of titanium and titanium alloys.

14. The prosthesis as claimed in claim 1, wherein said body is made of a material selected from the group consisting of titanium and titanium alloys.

15. The prosthesis as claimed in claim 1, wherein said liquid comprises water.

16. The prosthesis as claimed in claim 1, further comprising a pocket of gas provided inside said chamber and in said liquid.

17. The prosthesis as claimed in claim 1, wherein said body is movable freely within said chamber and relative to said opposing plates.

18. The prosthesis as claimed in claim 1, wherein movement of said opposing plates relative to one another is dampened by circulation of said liquid through said cavities of said body.

19. The prosthesis as claimed in claim 1, wherein said opposing plates are compressible toward one another along a main axis of compression.

20. The prosthesis as claimed in claim 19, wherein said flexible seal normally maintains said opposing plates at a first spaced distance relative to one another when no compression forces are applied to said plates.

21. The prosthesis as claimed in claim 20, wherein said opposing plates are compressible to a second spaced distance that is less than said first spaced distance when compression forces are applied to said opposing plates.

22. The prosthesis as claimed in claim 21, wherein the spaced distance of said plates relative to one another as a function of the compression forces applied to said plates follows a graph curve having a hysteresis form.

23. An intervertebral disc prosthesis comprising:

two opposing plates movable relative to one another, at least one of said plates including a securing element for securing said prosthesis to bone;

a flexible seal extending between said two opposing plates for forming a fluid-tight chamber between said two opposing plates;

a liquid provided in said fluid-tight chamber and between said opposing plates, wherein said plates are adapted to transfer compressive energy to said liquid when said plates move toward one another;

a porous body disposed in said fluid-tight chamber, said porous body having a plurality of pores at an outer surface thereof and cavities extending from said pores into said body, wherein the compressive energy transferred to said liquid when said plates move toward one another forces at least some of the liquid into the cavities of said body.

24. The prosthesis as claimed in claim 23, wherein the energy in said liquid is transferred to said body as the liquid is forced into said cavities.

25. A method of damping movement of opposing plates of an intervertebral disc prosthesis comprising:

providing the intervertebral disc prosthesis including two opposing plates, a flexible seal extending between said two plates for forming a closed chamber between said two plates, a liquid in said closed chamber, a porous body having internal cavities disposed in said chamber and said liquid, wherein said body and said liquid are selected so that said liquid does not normally wet to the cavities of said body;

applying compressive forces on said plates for moving said plates toward one another, transferring the compressive forces to said liquid for forcing said liquid into the cavities of said body, wherein said liquid stores at least some of the compressive force applied to said liquid through compression of said plates.

26. The method as claimed in claim 25, further comprising:

removing the compressive forces on said plates, whereupon the liquid in said cavities recedes from said cavities and returns to said chamber.

* * * * *

UNITED STATES PATENT AND TRADEMARK OFFICE
CERTIFICATE OF CORRECTION

PATENT NO. : 6,395,032 B1
DATED : May 28, 2002
INVENTOR(S) : Fabien Gauchet

It is certified that error appears in the above-identified patent and that said Letters Patent is hereby corrected as shown below:

<u>Column 4,</u>
Line 30, change "2" to -- 1 --.

Signed and Sealed this

Twenty-second Day of October, 2002

Attest:

Attesting Officer

JAMES E. ROGAN
*Director of the United States Patent and Trademark Office*